United States Patent [19]

Shapiro et al.

[11] Patent Number: 5,425,367
[45] Date of Patent: Jun. 20, 1995

[54] CATHETER DEPTH, POSITION AND ORIENTATION LOCATION SYSTEM

[75] Inventors: Alan R. Shapiro; Donald A. Kay, both of Sharon; Clair L. Strohl, Jr., Norfolk, all of Mass.

[73] Assignee: Navion Biomedical Corporation, Stoughton, Mass.

[21] Appl. No.: 755,024

[22] Filed: Sep. 4, 1991

[51] Int. Cl.⁶ .......................... A61B 5/05; A61B 19/00
[52] U.S. Cl. ..................... 128/653.1; 128/899; 324/326; 600/11
[58] Field of Search ................. 128/653.1, 899; 324/326, 322; 600/11-14

[56] References Cited

U.S. PATENT DOCUMENTS

| | | | |
|---|---|---|---|
| 3,932,805 | 1/1976 | Abe et al. | 324/309 |
| 4,173,228 | 11/1979 | Van Steenwyk et al. | 128/653.1 |
| 4,317,078 | 1/1982 | Weed et al. | 128/653.1 X |
| 4,379,261 | 4/1983 | Lakin | 324/233 |
| 4,445,089 | 4/1984 | Harrison | 324/328 |
| 4,572,198 | 2/1986 | Codrington | 128/658 X |
| 4,809,713 | 3/1989 | Grayzel | 128/785 |
| 4,905,698 | 3/1990 | Strohl, Jr. et al. | 128/653.1 |
| 5,005,592 | 4/1991 | Cartmell | 128/899 |
| 5,014,008 | 5/1991 | Flowerden | 324/326 |
| 5,042,486 | 8/1991 | Pfeiler et al. | 128/653.1 |
| 5,099,845 | 3/1992 | Besz et al. | 128/653.1 |
| 5,183,045 | 2/1993 | Takamura et al. | 128/653.2 |
| 5,196,796 | 3/1993 | Misic et al. | 324/322 |

Primary Examiner—Jerome L. Kruter
Assistant Examiner—Elizabeth Burke
Attorney, Agent, or Firm—Brian M. Dingman

[57] ABSTRACT

A system for externally locating the depth and orientation of a catheter in tissue with an external probe which generates a virtual rotating magnetic field. The catheter includes an inductive coil for developing an induced signal in response to the virtual rotating magnetic field. An indicating device such as a light bar display or digital readout indicates the strength of the induced signal for locating, independently of the relative angular orientation of the probe and the catheter, the depth in the tissue of the catheter.

35 Claims, 7 Drawing Sheets

CATHETER DEPTH, POSITION AND ORIENTATION LOCATION SYSTEM

FIELD OF INVENTION

This invention relates to a system for locating the depth, orientation and position of a catheter inside biological tissue.

BACKGROUND OF INVENTION

In today's practice of medicine, catheters are routinely required to be positioned inside the human body. Catheters are frequently hollow tubes that infuse fluids into or extract fluids from body organs. Catheters may also contain conductive wires for delivering electrical impulses, such as pacemaker wires, or contain devices for sensing physiological functions such as temperature, blood pressure, and cardiac output. Catheters may contain optical fibers for observing the interiors of body organs. A catheter may also be solid, such as a guide wire which is used to direct other catheters into body orifices, incisions or vessels.

Typically, catheters may be placed in the cardiovascular system, the digestive tract, the respiratory system, soft tissue, or other internal systems such as the excretory system. In most instances, catheters are placed using fluoroscopy or x-ray as a guide both during the procedure and as a confirmation that the device has been properly positioned. However, because of the cost of the equipment, fluoroscopy and x-ray are generally available only in the high cost operating room setting or in special procedure laboratories. Furthermore, there is a real concern about the repeated exposure of physicians, nurses and technicians to excessive radiation because of the multiple exposures required during placement and confirmation.

Two approaches to resolving these problems are disclosed in Van Steenwyck et al., U.S. Pat. No. 4,173,228, and Strohl, Jr., et al., U.S. Pat. No. 4,905,698. Van Steenwyck et al. disclose a catheter locating device which employs a sensing coil of wire embedded in the tip of a catheter tube, with the two coil wires brought out of the catheter to an external amplifier and detector circuit. The external probe contains two electromagnetic coils, one parallel to the skin (hereinafter called horizontal because the patient is generally in a supine position) and the other perpendicular to the skin (hereinafter called vertical), each driven by an electronic oscillator so that a high frequency, time-varying magnetic field is generated by either coil. The device has a switch for alternately energizing one or both of the coils. The sensing coil in the catheter senses the strength of the magnetic field generated by the horizontal (parallel) external coil, and the phase of the field generated by the vertical (perpendicular) external coil. The field strength at the sensor coil is inversely related to the distance between the horizontal coil and the sensor coil. The relative phase between the vertical coil drive signal and the sensed signal is indicative of the position of the vertical coil in relation to the sensor coil; the signals are in phase when the vertical coil is behind the sensor coil, the signals are out of phase when the vertical coil is in front of the sensor coil, and there is no induced signal in the sensor coil when the vertical coil is directly over the sensor coil.

Although the Van Steenwyck et al. device can relatively accurately locate the orientation and position of the catheter, it has a number of disadvantages which make it difficult and time consuming to use in the clinical setting. First, the device requires repeated scans with the probe parallel, then perpendicular, then rotated relative to the axis of the catheter. Further, the technique requires marking several external probe positions on the patient's skin and drawing a connecting line between them in order to establish the position of the sensor. Finally, the device requires switching repeatedly between the two external coils in order to verify the position and direction of the catheter sensor coil. Between 8 and 12 separate steps are necessary in order to establish the catheter position and direction. Furthermore, no quantitative indication of depth is given by the Van Steenwyck et al. device. The depth of the catheter below the surface of the skin can only be inferred from the signal strength displayed on the meter and from the setting of the range-selector switch.

SUMMARY OF INVENTION

It is therefore an object of this invention to provide a system which is simple and easy to use for externally locating the position, angular orientation and depth of a catheter.

It is a further object of this invention to provide such a system which does not require repeated scans in a number of different directions.

It is a further object of this invention to provide such a system which does not require marking probe positions on the patient's skin.

It is a further object of this invention to provide such a system which does not require the operator to switch between coils.

It is a further object of this invention to provide such a system which completely eliminates the need for x-ray or fluoroscopy guidance during catheter placement.

It is a further object of this invention to provide such a system which gives a numerical display of the depth of the catheter below the skin, and a display indicating the direction in which the catheter is pointing.

This invention accomplishes the above objects, that is, an effective, easy to use catheter location system, by providing a pair of mutually perpendicular, coplanar, horizontal (parallel to the skin) electromagnetic coils driven in quadrature (90° phase between alternating current supplied to each coil) to generate a rotating magnetic field which rotates once during each cycle of the driving frequency so that the strength of the signal induced in the catheter sensor coil is independent of the relative angle between the probe axis in its horizontal plane and the angle of the sensor coil axis in its horizontal plane, but is dependent on the distance between the probe and the sensor coil. When the probe is directly over the sensor, the strength of the signal induced in the sensor is related to the actual depth of the sensor below the probe.

This invention features a system for externally locating the depth and orientation of a catheter in tissue which includes an external probe having means for providing a virtual rotating magnetic field, a sensor in the catheter for developing an induced signal in response to the virtual rotating magnetic field, and means for indicating the strength of the induced signal for locating, independently of the relative angle of orientation of the probe and the sensor, the depth in the tissue of the catheter.

Preferably, the virtual rotating magnetic field is provided by two mutually perpendicularly oriented electromagnetic coils in the probe which are horizontal (parallel to the supine patent's skin), coplanar, and wound on a unitary core. Those coils may then be driven in quadrature to accomplish a virtual rotating magnetic field of substantially constant strength.

The sensor preferably includes an inductive coil. The means for indicating the relative strength of the induced signal may include a light bar display, a digital display, or an audio output in which either the tone or volume is varied in relation to the induced signal strength. There may further be included a means for displaying the peak induced signal strength.

The system may also include means for resolving the relative angular orientation of the probe and the catheter, which may be accomplished by comparing the phase of a coil drive signal to the phase of the induced signal. Preferably, there are means for visually indicating the resolved angular orientation, which may be provided on the probe itself. That may be accomplished by a plurality of lights arranged on the probe in a circular pattern in which a single light indicative of the relative angular orientation of the probe and the sensor is lit.

The system may further include means for resolving the direction of the catheter in relation to the probe, which may be accomplished with a third, vertically oriented electromagnetic coil and means for driving that coil with an AC signal to create time-varying magnetic field. The means for resolving the direction of the catheter may then further include means for comparing the phase of the AC signal to the phase of the induced signal. There may be included means on the probe for visually indicating the resolved direction of the catheter in relation to the probe.

The system may further includes means for multiplexing the coil pair vertical coil drive signals to save power. In addition, the sensor may include a plurality of inductive coils spaced along the catheter for separately developing induced signals to locate different portions of the catheter with a single external probe.

DISCLOSURE OF PREFERRED EMBODIMENT

Other objects, features and advantages will occur to those skilled in the art from the following description of a preferred embodiment and the accompanying drawings in which.

Figure 1:
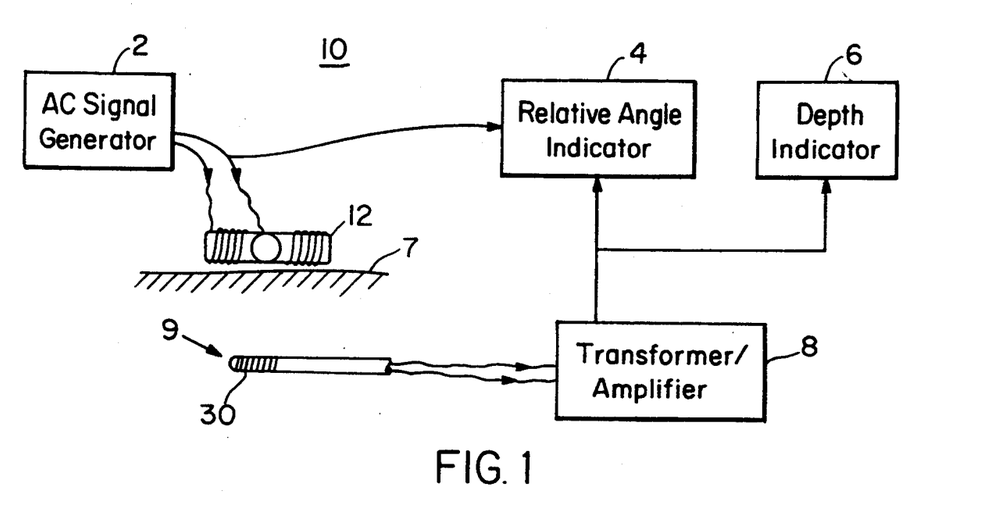
FIG. 1 is a schematic block diagram of the catheter locating system according to this invention.

There is shown in FIG. 1 catheter depth and position locating system 10 according to this invention. System 10 includes cross-shaped coil set 12 on which are wound two mutually perpendicular coils of wire driven by alternating high frequency current from generator 2 to generate a high-frequency magnetic field. The coils of coil set 12 are driven in quadrature to create a rotating magnetic field which rotates through 360° once during each cycle of the driving frequency to provide a field of essentially constant strength. As a result, the signal induced in sensor coil 30, coaxial with catheter 9, and located below the level of skin 7, will have a strength dependent only on the distance from coil set 12, and independent of the axial direction of the coils of coil set 12 in relation to coil 30. The coils of coil set 12 may be wound over an iron or ferrite core to strengthen the magnetic field, or may have no core.

The signal induced in sensor coil 30 is fed to transformer/amplifier 8, which in turn sends the amplified signal to relative angle indicator 4 and depth indicator 6. The signal induced in coil 30 is a function of the strength of the field created by the coils of coil set 12, but is independent of the relative horizontal angle between coil set 12 and coil 30. Relative angle indicator 4 indicates the relative angle between the axis of one of the coils of set 12 and the axis of coil 30 in response to the phase difference between one of the coil drive signals and the sensed signal, as is further described below in conjunction with FIG. 3.

Figure 2A:
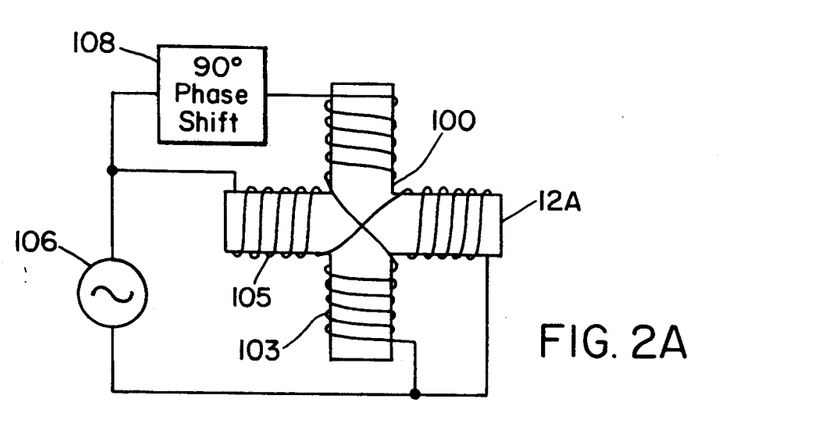
FIG. 2A is a schematic diagram of the horizontal field generating coils and quadrature drive of the system of FIG. 1.

Coil set 12a, FIG. 2A includes cross-shaped coil form 100 on which are wound perpendicular, coplanar coils 103 and 105. Coil 105 is driven by high frequency alternating current source 106; coil 103 is driven by the same source phase-shifted 90° to drive the coils in quadrature for providing a virtual rotating magnetic field which rotates 360° during each cycle of source 106. This arrangement is essentially an electronic version of a rotating magnetic field created by a mechanically rotated bar magnet. The result is a field of essentially constant strength, and so an induced signal of constant strength when the catheter is at a particular depth, regardless of the angle in the horizontal plane between the axis of either coil 103 or coil 105, and the axis of catheter coil 30, FIG. 1. Because the horizontal orientation of the probe is not significant, the catheter location procedure is greatly simplified over that described in U.S. Pat. No. 4,173,228.

Figure 2B:
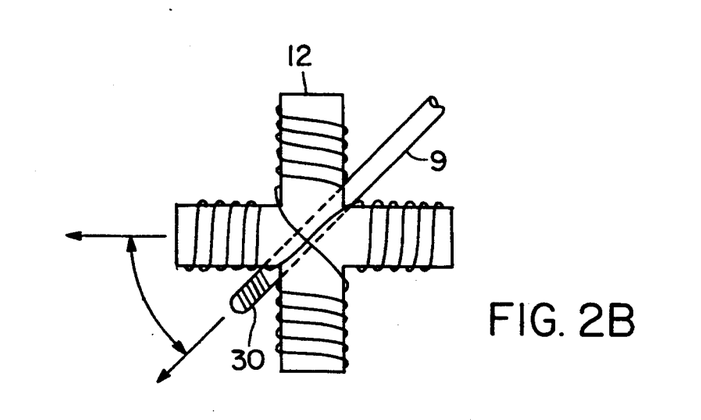
FIG. 2B is an overhead view of the horizontal field-generating coils and the catheter sensor coil.
Figure 2C:
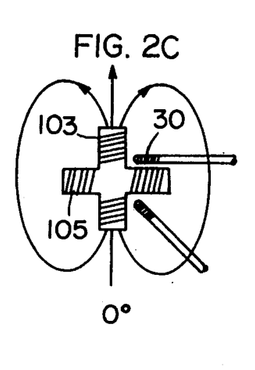
FIGS. 2C through 2K are diagrams of the horizontal field-generating coils, showing the rotating magnetic field and the induced sensor voltages.
Figure 2D:
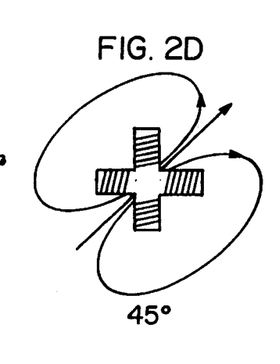
Figure 2E:
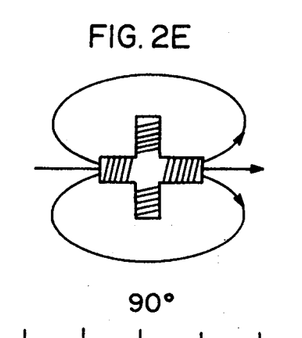
Figure 2F:
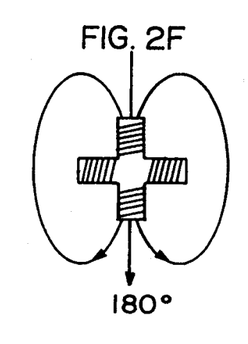
Figure 2G:
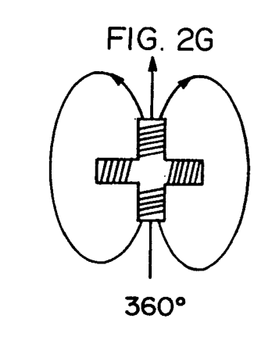
Figure 2H:
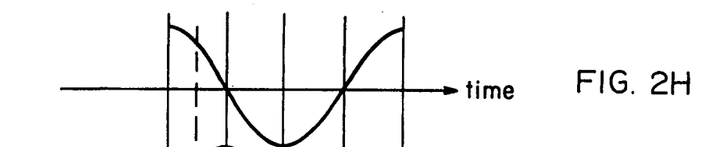
Figure 2I:
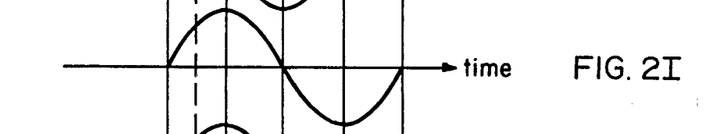
Figures 2J, 2K:
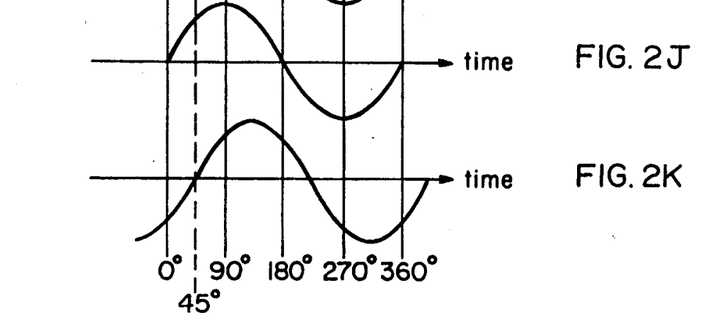

FIG. 2B shows a top view of the driven coil set 12 and the catheter 9 and the sensor coil 30, showing the relative horizontal angle between the axis of coil set 12 and sensor coil 30.

FIGS. 2C through 2K show how the quadrature currents in mutually perpendicular coils 103 and 105 generate a rotating magnetic field. Approximately one cycle of the driving current is shown. At 0° the currents in coils 103 and 105 generate a field which points to the top of the page, inducing no voltage in sensor coil 30 when it is at angle A, but at 90° the sensor voltage is maximum positive, and at 270° is at maximum negative. When the sensor is physically at angle B relative to coil 103, the maximum positive and negative induced voltage has the same value as at angle A, but it is phase shifted in time by B-A degrees. Thus, the amplitude of the induced sensor voltage is independent of angular orientation, but the phase of the induced voltage is directly related to the physical angle between coil 103 and sensor coil 30.

Figure 2L:
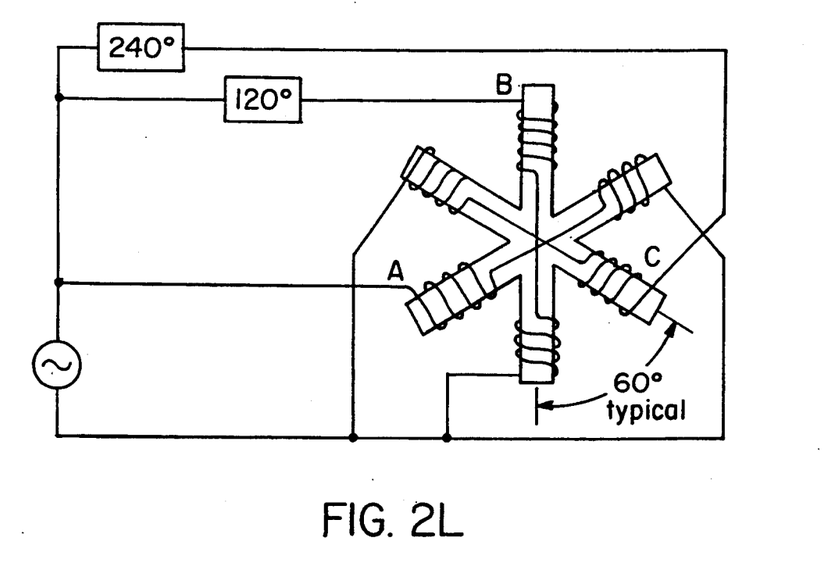
FIG. 2L is a three coil alternative to the coil set of FIG. 2A.

Although a cross-shaped coil is shown in FIG. 2A, other shapes and configurations may occur to one skilled in the art. For example, a star-shaped coil form as shown in FIG. 2L could be driven by three alternating current sources (A,B and C) with B phase-shifted by 120 degrees and C by 240 degrees. This configuration would also produce a rotating magnetic field of constant strength.

Figure 3:
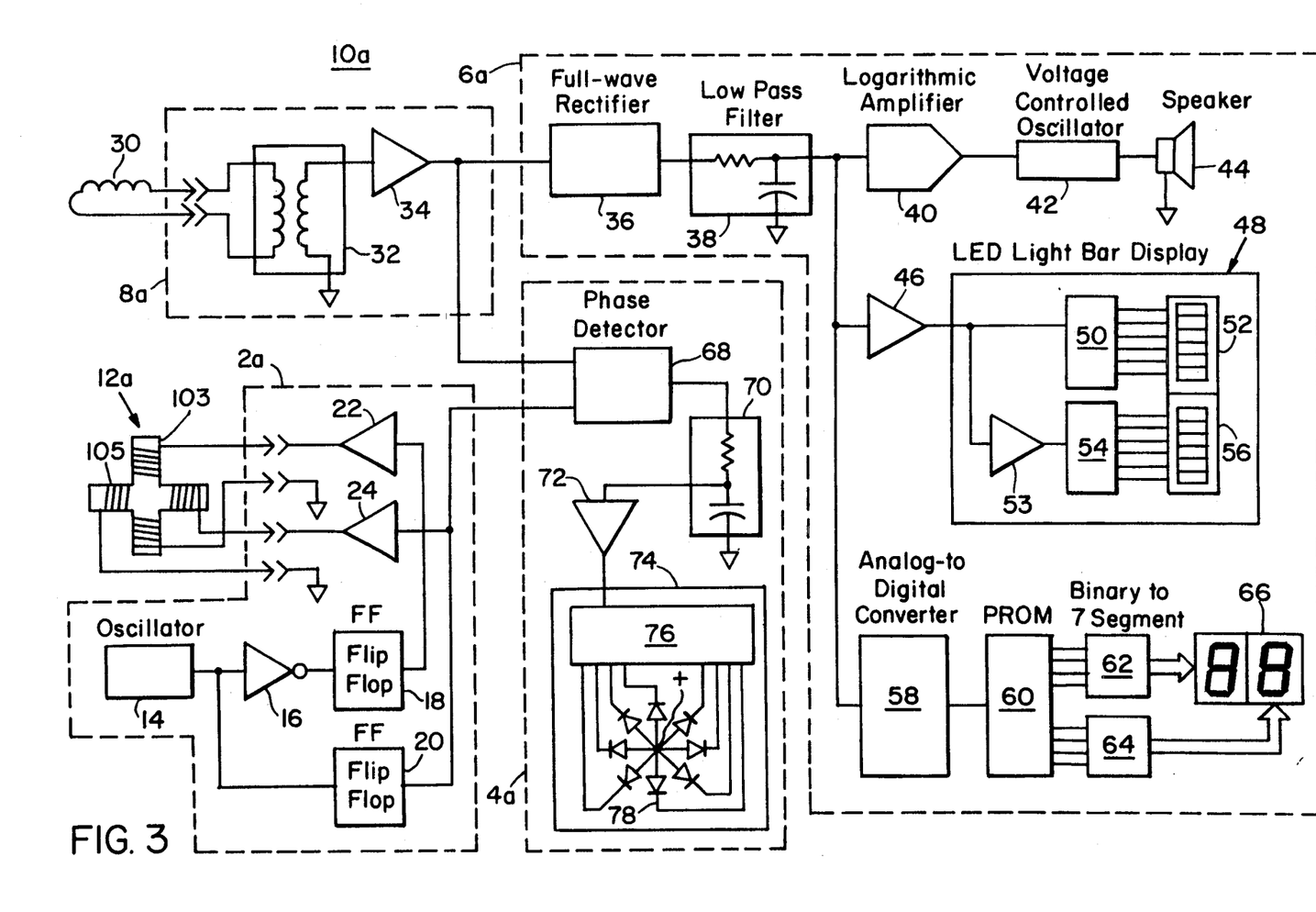
FIG. 3 is a more detailed schematic diagram of the system of FIG. 1.

One embodiment of system 10 of FIG. 1 is shown in FIG. 3. System 10a includes alternating current signal generator 2a for driving perpendicular coils 103 and 105 in quadrature. Generator 2a includes high frequency oscillator 14 which, in combination with inverter 16, flip-flops 18 and 20, and switches or current amplifiers 22 and 24, provides a high frequency alternating current signal to identical coils 103 and 105 to drive the coils in quadrature as explained above. This magnetic fields induces a signal in sensor coil 30 which is proportional to the inverse cube of the distance of the sensor from transmitter coil 12. The sensor voltage is stepped up by transformer 32, which also provides safety isolation between patient and circuitry, and is amplified by amplifier 34. The amplified signal is provided both to relative angle indicator 4a and depth indicator 6a.

Depth indicator circuitry 6a includes full wave rectifier 36 and low pass filter 38 which provide a dc voltage, inversely proportional to the cube of the distance of the sensor from the field generating coils, to one or more of the audio and visual outputs for indicating the actual or relative depth of the sensor coil 30 in relation to the field generating coils 103 and 105. One audio output may be provided by employing logarithmic amplifier 40 for driving voltage controlled oscillator 42 whose output is applied to speaker 44 to provide an audible tone whose pitch increases as the probe gets closer to the sensor coil. The desirability of a logarithmic amplifier will be explained below. Another display can be LED or liquid-crystal light bar display 48, in which the length of the bar increases as the probe is brought closer to the sensor coil.

Display 48 preferably incorporates a logarithmic as opposed to a linear display of the sensor voltage to accommodate the wide range of sensor voltages. As an example, the depth of the sensor inside the body could vary from less than ½ inch to more than 7 inches, depending on the patient and the catheter location. Over this range, the amplified sensor output voltage could range, as an example, from less than 1 millivolt to over 500 millivolts, a range of 500 to 1. Linear displays can adequately display a range of no better than about 30 to 1; any voltage smaller than 1/30th of fullscale would be barely visible. By using such a logarithmic display, the upper portion of the indicator is compressed and the lower portion expanded so that a voltage level of 1/500th of full scale would appear in the same position as a level of 1/10th of full scale on a linear display, thus allowing the location apparatus to be usable over a larger range of catheter depths in the body. The light bar display may be accomplished with drivers 50 and 54 which may be an LM3915 logarithmic bar graph display driver made by National Semiconductor Corporation, each having ten outputs, for driving LED light bar displays 52 and 56. Each LED represents a change in sensor voltage of 3 decibels. 20 LEDs represents a 60 decibel change, which is a 1000 to 1 change in sensor voltage. A scale in inches or centimeters may be marked beside the LEDs, indicating the relative depth of sensor 30.

Likewise, the use of a logarithmic amplifier 40 to drive voltage-controlled oscillator 42 results in a smooth and gradual change in pitch as the sensor signal varies over the range of 500 to 1.

A third display may be created by having the signal-receiving circuitry generate a DC voltage related to the strength of the sensed signal, which is then converted to digital form by analog-to-digital converter 58. The digital data is provided to a programmable read-only memory circuit 60, which acts as a "look-up table" and converts the digital data to a two or three digit numerical display representing the distance between the external probe coil and the catheter sensor coil, using drivers 62 and 64 which convert binary data to voltages that drive 7-segment numerical LED or Liquid Crystal displays.

Relative angle indicator 46a indicates the approximate relative angle in the horizontal plane between the axis of one of the two electromagnetic coils of field-generating coil set 12 and the axis of sensor coil 30 by applying the coil drive signal and the amplified sensed signal to phase detector 68. The output of phase detector 68 is filtered by low pass filter 70, amplified by amplifier 72, and provided to relative angle display 74 which includes display driver 76 for driving eight light-emitting diodes or lamps physically arranged around the periphery of a circle. Display driver 76 may be a LM3914, made by National Semiconductor, a bar graph display driver which converts an analog input voltage to discrete drive voltages for up to 10 LEDs. Although only 8 LEDs are shown in display 74, a larger number could be incorporated by adding more display drivers 76. The result, as shown with more particularity below in conjunction with FIGS. 6 and 7, is a visual indication of the approximate relative angular orientation between the long axis of the probe housing coil set 12a and the axis of the catheter sensor coil, thereby allowing the person placing the catheter to determine the exact position of the catheter tip without the use of fluoroscopy or x-ray during the positioning.

Figure 4A:
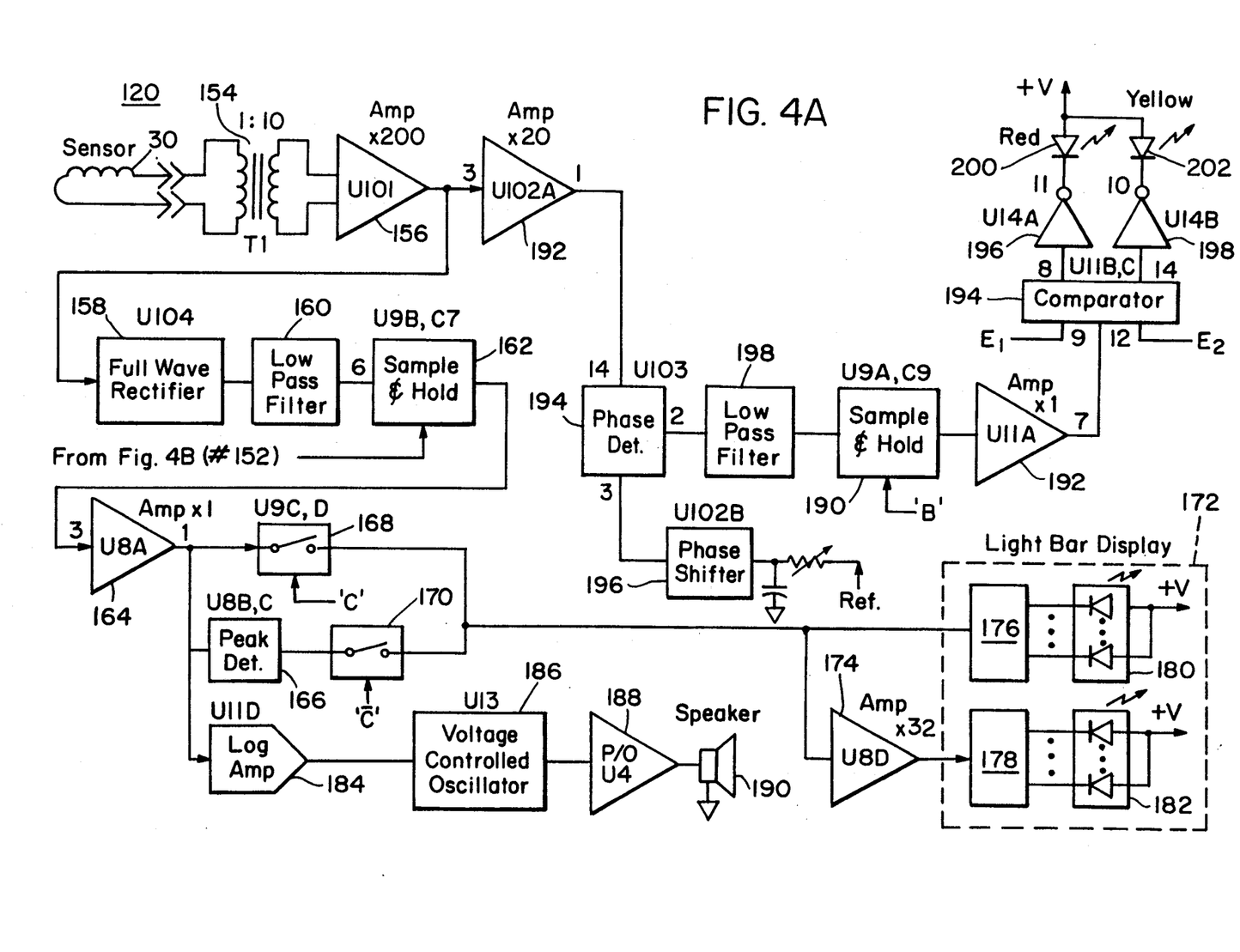
FIG. 4 is a still more detailed schematic diagram of an alternative embodiment of the system of this invention which additionally employs a vertical field generating coil for indicating whether the probe is in front of, directly over, or behind the sensor coil.
Figure 4B:
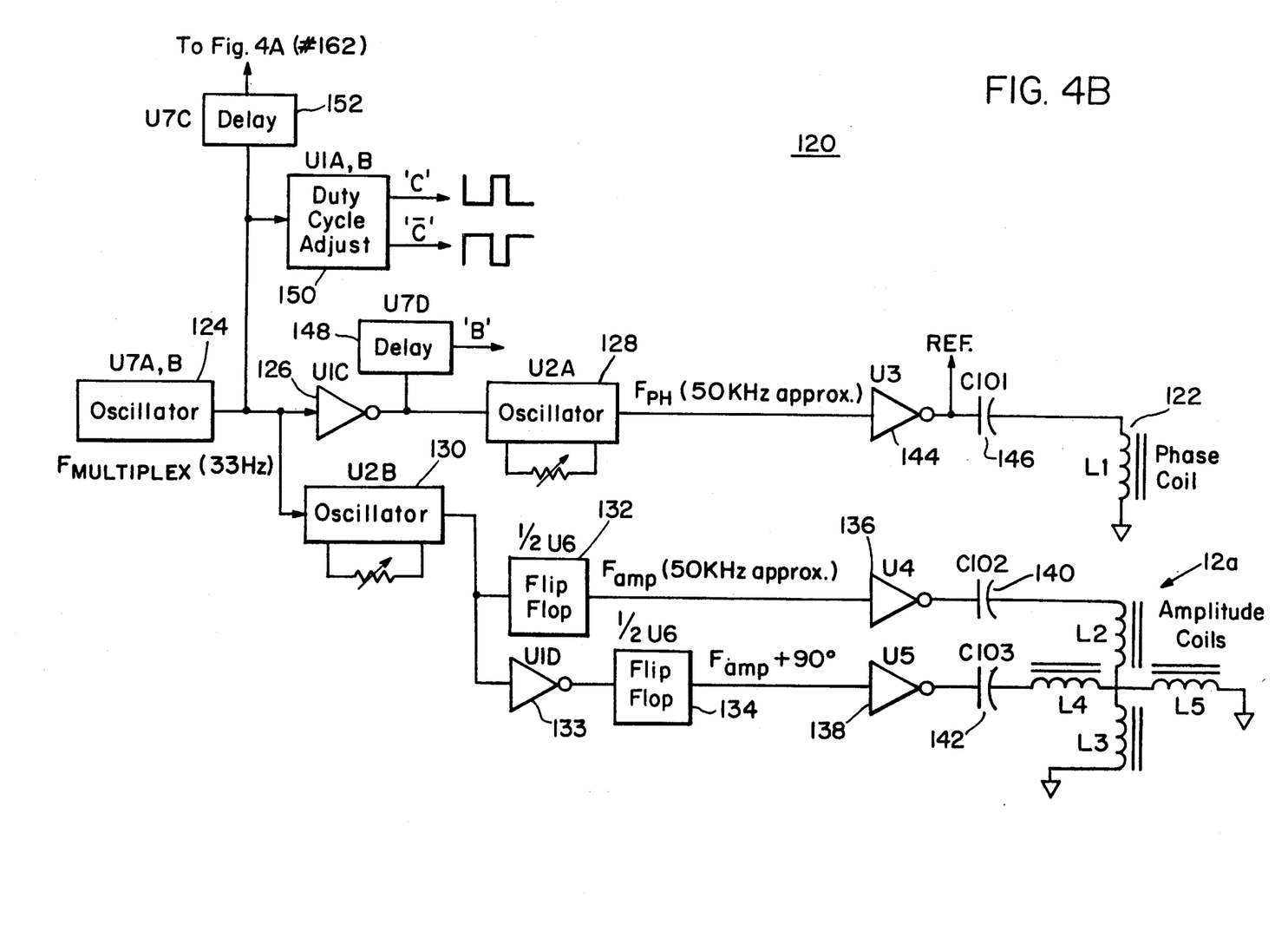

FIGS. 4A and 4B together (FIG. 4) depicts an alternative embodiment of the system of this invention employing a vertically-oriented field-generating coil in conjunction with the horizontal coil pair described above for additionally providing the relative orientation between the external probe and the catheter sensor coil; that is, whether the field-generating coil is in front of, behind, or directly over the sensor coil. In addition, FIG. 4 depicts multiplexing of the coil drive signals to save battery power.

The system of FIG. 4 combines the use of a vertically oriented field-generating coil for generating a phase-sensitive response in the catheter sensor coil, and a horizontally-oriented field-generating coil for creating an amplitude-sensitive response in the sensor coil. In order to avoid switching manually between the two techniques, a multiplexing scheme is employed, in which the horizontal and vertical field-generating coils are alternately energized. Likewise, the received signals are alternately sampled-and-held in synchronism with the field-generating coils so that two separate DC signals are developed, one related to the phase between the field of the vertical coil and the sensor signal, and the second proportional to the amplitude (intensity) of the field of the horizontal coil as received by the sensor coil.

The drive signal multiplexing is accomplished with low frequency 33 hertz square wave oscillator 124 which during its positive half cycle enables high-frequecy oscillator 130 and, through inverter 126, enables high-frequency oscillator 128 on the alternate half cycle to drive the amplitude coils 12a and phase coil 122 at alternating 15 millisecond intervals.

Phase detection between vertical phase coil 122 and sensor coil 30 is accomplished by driving MOSFET switch 144 with the output of oscillator 128, preferably approximately 50 kilohertz. This output is also provided as the phase reference signal input to phase shifter 196, described below. Switch 144 switches current to the resonant circuit comprising capacitor 140 and the vertical field-generating coil 122.

The magnetic field created by coil 122 induces a voltage in sensor coil 30. The sensor voltage is stepped-up by transformer 154, which also isolates the sensor from the remaining circuitry, and is then amplified 200 times by amplifier 156. The signal is amplified 20 times additionally by amplifier 192, and fed to the signal input of phase detector 194. The phase detector reference signal is fed from the output of switch 144 to the reference input of phase detector 194 through phase shifter 196, which is adjusted to compensate for phase shifting of the input signal created by the amplifier circuitry.

The output of phase detector 194 is a high frequency signal which is mostly high when the signals are in phase, and mostly low when the signals are out of phase, regardless of the signal strength. The phase detector output goes through low pass filter 198 which smoothes the high frequency signals to DC and then to sample and hold circuit 190, which is enabled by a delayed hold pulse from delay circuit 148 to ensure that the phase detector output has settled to its final value before the sample and hold 190 is enabled. Unity gain amplifier 192 presents a high impedance to sample and hold 190. The signal is then passed to comparator 194 which is supplied with two reference voltages. When the sensed and reference signals are in phase, the output of amplifier 192 is high and the output of comparator 194 at pin 8 goes high, causing inverter 196 to turn on the red LED. When the field-generating coil position is changed such that the signals are 180° out of phase, the output of amplifier 192 is low, causing comparator 194 output to go high at pin 14, causing inverter 198 to turn on yellow LED 202. When the sensor output signal is very weak or non-existent, the output of amplifier 192 assumes a midway voltage so that neither comparator in comparator circuit 194 is tripped, and neither LED is lit. The result is that when the vertical phase coil 122 is beyond sensor coil 30, that is located somewhere along the length of the catheter not quite to its tip, the transmitted and sensed signals are in phase, causing the red LED to light. When the transmit coil is before the sensor coil, the yellow LED lights. When the device switches between the red and yellow LED, transmit phase coil 122 is directly over sensor coil 30.

Amplitude detection (distance determination) of system 120 is accomplished as follows. Oscillator 130 drives flip-flops 132 and 134 such that the square wave output of flip-flop 134 is shifted 90° from that of flip-flop 132. The square waves drive MOSFET switches 136 and 138 which switch current into the resonant circuit created by capacitor 140 and colinear amplitude coils L2 and L3, and the resonant circuit created by capacitor 142 and collinear coils L4 and L5, which are coplanar and perpendicular to coils L2 and L3 as shown above in conjunction with FIG. 2A to provide a rotating magnetic field rotating at the approximately 50 kilohertz drive frequency. The amplitude of the signal induced in sensor coil 30 is thus proportional to the inverse cube of the distance between coils 12a and coil 30 regardless of the angular orientation in the horizontal plane between either of the coils in coil 12a and coil 30.

The amplified sensor voltage is provided to full wave rectifier 158, and is then filtered and fed to sample and hold circuit 162. Sample and hold circuit 162 is enabled by a delayed hold pulse from delay 152, which allows the rectified, filtered signal to settle to its final value before it is sampled and held to provide, at the output of unity gain amplifier 164, a DC voltage representative of the distance between the drive coil and the sensor coil. This DC signal is applied to switch 168 and peak detector 166, whose output is supplied to switch 170. Switches 168 and 170 are driven by duty cycle adjust circuit 150 which provides signal C to switch 168 and the complementary signal to switch 170 so that switch 168 is on approximately three times longer than switch 170, resulting in a brighter light intensity in light bar display 172 for the currently-sensed amplitude light bar than for the peak light bar. The peak remains lit at a low intensity so that the user may know the absolute peak encountered, and thus easily find the probe position in which the amplitude field-generating coils are closest to the sensor coil. The outputs are provided to lightbar display 172 which preferably includes 20 LED segment outputs 180 and 182, each driven by drivers 176 and 178.

An alternative or additional audio output is accomplished by feeding the DC signal from amplifier 164 to logarithmic amplifier 184 whose output is applied to voltage controlled oscillator 186, driving speaker 190 through amplifier 188. In this case, the pitch of the speaker tone changes as the probe coil is moved in relation to the sense coil, with the highest pitch indicating closest proximity.

The result of the system shown in FIG. 4 is the simultaneous detection of the depth of the sensor coil and the relative position of the probe and the sensor coil, allowing the user to locate the exact position and depth of the catheter tip by scanning in one direction on the skin of the patient, along the estimated direction of the catheter, until a signal maximum is displayed, and then moving the probe along a line perpendicular to the direction of the first scan until an absolute maximum is displayed, indicating the closest position from the probe to the sensor coil. If the user moves the probe away from the point of maximum indication, the peak light bar segment will be dimly lit by the peak detector circuit, thereby informing the user to return the probe to the point of maximum indication. The phase detection in conjunction with the red and yellow lights is employed to confirm that the probe is directly over the catheter coil. The relative angular positioning of FIG. 3 may also be used to provide the relative direction of the sensor coil axis in relation to the probe axis so that the user may determine if the catheter tip is facing in the correct direction or has doubled back on itself.

Following is a Component parts list for the embodiment of FIG. 4:

| Component No. | Description | Type No. |
| --- | --- | --- |
| U101 | Operational amplifier | LF357 |
| U102, U104 | Op. amp., dual | TL052 |

| Component No. | Description | Type No. |
| --- | --- | --- |
| U103, U13 | Phase detector, Voltage-controlled oscillator | CD4046 |
| U1 | Quad NOR gate | CD4001 |
| U2 | Dual Oscillator | ICM7556 |
| U3, U4, U5 | Quad MOSFET | VQ7254J |
| U6 | Dual D Flip-Flop | CD4013 |
| U7 | Quad NAND gate | CD4011 |
| U8, U11 | Op.amp.,quad | TL034 |
| U9 | Analog switch, quad | DG441 |
| U10, U12 | Not used | |
| U14 | Inverter | CD4049 |
| 176,178 | Logarithmic Bar Graph Driver | LM3915 |

Figure 5:
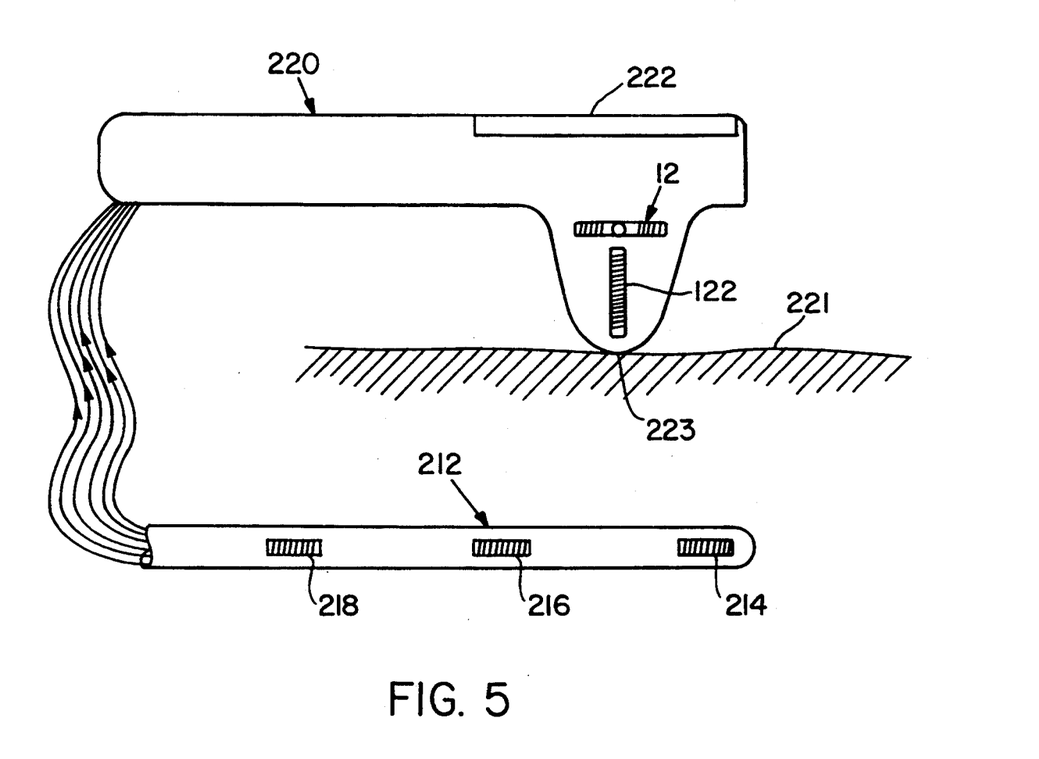
FIG. 5 is a simplified diagram of one form of the probe of this invention in use, sensing the location of a catheter with a plurality of sense coils.

One physical embodiment of the probe and catheter system of this invention is shown in FIG. 5. Probe 220 may include the power source and circuitry of the system and may have vertical coil 122 mounted proximate skin surface 221, with horizontal coil set 12 mounted directly thereabove. Catheter 212 may include one or more of sensor coils 214, 216 and 218 for indicating the position of catheter 212 in relation to probe 220, specifically tip portion 223 of probe 220. When more than one sensor coil is employed in the catheter, the device may include a switch for manually switching from one sense coil to the next so that probe 220 may be used to detect not only the position of the tip of catheter 212, but also some distance along its length back from the tip to indicate the catheter path. Alternatively, the sensor coils may be multiplexed in some manner to alternately employ their outputs for the same purpose.

Figures 6A, 6B:
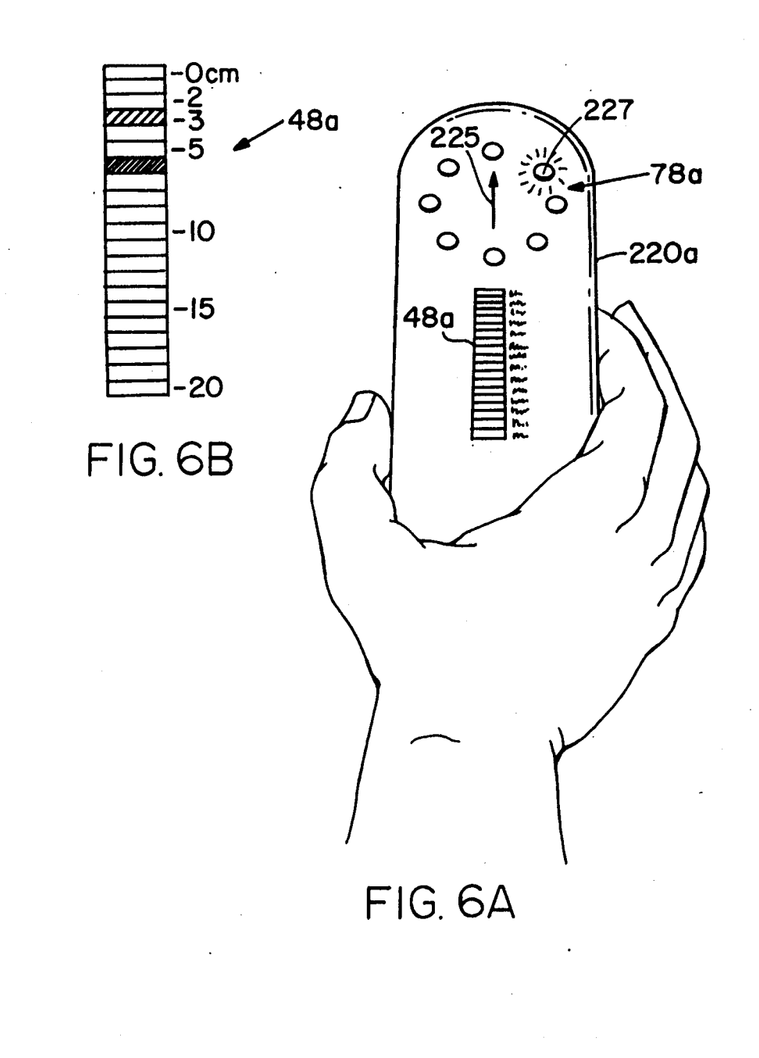
FIGS. 6A and 6B together are a top plan view, partially enlarged, of one form of a probe according to the invention similar to that shown in FIG. 5.
Figure 7:
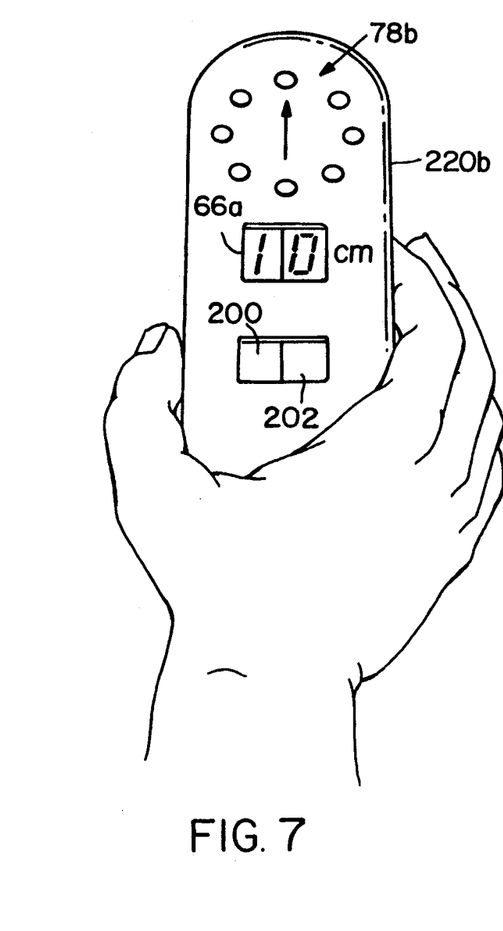
FIG. 7 is a top plan view of an alternative to the probe of FIG. 6.

FIGS. 6 and 7 depict in simplified form displays 222 of two different embodiments of the probe according to this invention. Probe 220a, FIGS. 6A and 6B, includes circular LED display 78 for indicating the relative horizontal angle between the probe and sensor coil. Arrow 225 embossed on probe 220a is axially aligned with the one of the coils of horizontal coil 12 which is used to provide a phase detection reference signal as described above. Then, when one of the LEDs of display 78a, for example LED 227, is lit, it indicates the relative angle of the axis of the sensor coil in relation to the probe axis as indicated by arrow 225. Thus, in the example shown, the probe is indicating that the sensor coil, or catheter tip, is facing approximately northeast, or 45° in a clockwise direction from the direction of arrow 225. Finer angular resolution would be achieved if a higher number of LEDs were used. For example, with 20 LEDs each LED would represent an angular difference of 18 degrees. Lightbar display 48a provides an indication of the depth of the sensor coil. A numerical scale, in inches or centimeters, may be inscribed alongside display 48a to indicate the depth that each segment represents. Display 48a shows one segment brightly lit and the segment representing maximum sensor signal strength dimly lit.

An alternative display, probe 220b, FIG. 7, includes circular LED pattern 78b along with digital depth readout 66a of sensor depth, and red and yellow LEDs 200 and 202, respectively, for indicating the relative position of vertical coil 122, FIG. 5, in relation to the sensor coil as described above.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A system for externally locating a sensor in tissue, comprising:
    an external probe including electronic means for providing a horizontal rotating magnetic field;
    a sensor for placement in tissue at a relative distance from said probe and at a relative angular orientation, in a horizontal plane, to said probe, in which the sensor develops an induced signal having a relative strength in response to said rotating magnetic field;
    means for determining the relative strength of said induced signal, independently of the relative angular orientation in the horizontal plane of said probe and said sensor; and
    means, responsive to said means for determining the relative strength of said induced signal, for indicating the relative distance between said probe and said sensor.

2. The system of claim 1 in which said means for providing a horizontal rotating magnetic field includes two mutually-perpendicularly-oriented electromagnetic coils in said probe.

3. The system of claim 1 in which said coils are coplanar.

4. The system of claim 3 in which said coils are wound on a unitary core.

5. The system of claim 2 in which said means for providing a horizontal rotating magnetic field further includes means for driving said coils in quadrature to accomplish a horizontal rotating magnetic field of substantially constant strength.

6. The system of claim 1 in which said sensor includes an inductive coil.

7. The system of claim 6 in which said sensor includes a plurality of inductive coils spaced along a catheter for separately developing induced signals to locate different portions of the catheter with a single external probe.

8. The system of claim 1 in which said induced signal has a peak induced signal strength and said means for indicating the relative distance between said probe and said sensor includes means for displaying the peak induced signal strength.

9. The system of claim 1 in which said means for indicating the relative distance between said probe and said sensor includes means for generating a light bar display.

10. The system of claim 1 in which said means for indicating the relative distance between said probe and said sensor includes means for generating an audio tone having a frequency and a volume.

11. The system of claim 10 in which said means for indicating the relative distance between said probe and said sensor further includes means for varying the frequency of said audio tone in relation to the induced signal relative strength.

12. The system of claim 10 in which said means for indicating the relative distance between said probe and said sensor further includes means for varying the volume of said audio tone in relation to the induced signal relative strength.

13. The system of claim 1 further including means for resolving the relative horizontal angular orientation of said probe and said sensor.

14. The system of claim 13 in which said means for providing a horizontal rotating magnetic field includes at least one coil and a coil drive signal having a phase, and said induced signal has a phase, and said means for resolving the relative horizontal angular orientation of said probe and said sensor includes means for comparing the phase of said coil drive signal to the phase of said induced signal.

15. The system of claim 13 in which said sensor has a longitudinal axis lying along a direction in a horizontal plane, and further including means for visually indicating the true direction of the sensor axis in the horizontal plane.

16. The system of claim 15 in which said means for visually indicating the true direction of the sensor axis in the horizontal plane includes a plurality of lights arranged on said probe in a circular pattern having a center, and means, responsive to said means for resolving the relative horizontal angular orientation of said probe and said sensor, for lighting a single light whose direction relative to the center of the circular pattern is indicative of the true direction of said sensor axis in the horizontal plane.

17. The system of claim 15 in which said sensor has a distal end along the longitudinal axis, and in which said means for visually indicating the true direction of the sensor axis in the horizontal plane indicates the true direction of the sensor distal end along the longitudinal axis.

18. The system of claim 17 in which said means for visually indicating the true direction of the sensor axis in the horizontal plane includes a plurality of lights arranged on said probe in a circular pattern having a center, and means, responsive to said means for resolving the relative horizontal angular orientation of said probe and said sensor, for lighting a single light whose direction relative to the center of the circular pattern is indicative of the true direction of the sensor distal end along the longitudinal axis.

19. The system of claim 1 in which said sensor has a position in relation to said probe, and further including means for resolving the position of said sensor in relation to said probe.

20. The system of claim 19 in which said means for resolving the position of said sensor in relation to said probe includes a vertically-oriented electromagnetic coil in said probe, and means for driving said coil with an AC signal to create a time-varying magnetic field.

21. The system of claim 20 in which said AC signal and said induced signal have a phase, and said means for resolving the position of said sensor in relation to said probe further includes means for comparing the phase of said AC signal to the phase of said induced signal.

22. The system of claim 20 in which said means for providing a horizontal rotating magnetic field includes a field drive signal, and further including means for multiplexing the field drive signal and the vertically-oriented electromagnetic coil AC drive signal.

23. The system of claim 19 further including means on said probe for visually indicating the resolved position of said sensor in relation to said probe.

24. The system of claim 1 in which said means for indicating the relative strength of said induced signal includes a scale of inches or centimeters on said probe to provide a numerical indication of the relative distance between said sensor and said probe.

25. The system of claim 1 in which said means for providing a horizontal rotating magnetic field includes three coils on a six-pointed coil form driven by a 3-phase alternating current.

26. The system of claim 1 in which said means for indicating the relative strength of said induced signal includes an analog meter display.

27. The system of claim 1 in which said means for indicating the relative strength of said induced signal includes a digital numerical display.

28. The method of claim 1 in which said sensor is located coaxially within a catheter.

29. A system for externally locating a sensing coil in tissue, comprising:
an external probe having an axis and including a horizontally-oriented pair of perpendicular electromagnetic coils;
means for driving said pair of coils in quadrature with a drive signal having a phase to create a horizontal rotating magnetic field of substantially constant strength;
an inductive sensing coil at a relative distance from said probe and at a relative angular orientation, in a horizontal plane, to said probe, and having a distal end located in a true direction along a longitudinal axis for developing, in response to said rotating field, an induced signal having a phase and strength;
means, responsive to said induced sensing coil signal, for indicating the strength of the induced signal as a measure of the relative distance between the sensing coil and the probe, independently of the relative horizontal angular orientation of said probe and said sensing coil;
means for comparing the phase of the drive signal for one of the pair of coils to the phase of the induced signal; and
means, responsive to said means for comparing the phase of the drive signal for one of the pair of coils to the phase of the induced signal, for displaying the true direction of the sensing coil distal end along the longitudinal axis in the horizontal plane.

30. A system for externally locating a catheter in tissue, comprising:
an external probe having an axis and including a horizontally-oriented pair of perpendicular electromagnetic coils and a third, vertically-oriented electromagnetic coil perpendicular to said horizontally-oriented coils;
means for driving said pair of coils in quadrature with a drive signal having a phase to create a horizontal rotating magnetic field of substantially constant strength;
means for driving said third coil with an AC signal to create a time-varying magnetic field having a phase;
a catheter with a longitudinal axis at a relative horizontal angular orientation to said probe axis, and including an inductive sensing coil at a relative distance from said probe, and at a position in relation to said probe in the catheter tip, said tip located in a true direction in a horizontal plane along the longitudinal axis of the catheter, said sensing coil developing induced signals in response to said rotating and time-varying magnetic fields;
means, responsive to said sensing coil signal induced by said rotating field, for indicating the relative distance between the catheter sensing coil and the probe, independently of the relative horizontal angular orientation of said probe axis and said catheter axis;

means for resolving the phase difference between said time-varying magnetic field and the sensing coil signal induced by said time-varying magnetic field;

means, responsive to said means for resolving the phase difference between said time-varying magnetic field and the sensing coil signal induced by said time-varying magnetic field, for indicating the position of the sensing coil in relation to the probe;

means for comparing the phase of the drive signal for one of the coils of the coil pair to the phase of the signal induced in the sensing coil in response to said rotating magnetic field; and means, responsive to said means for comparing the phase of the drive signal for one of the coils of the coil pair to the phase of the signal induced in the sensing coil in response to said rotating magnetic field, for displaying the true direction of the catheter tip along the longitudinal axis in the horizontal plane.

31. A system for externally locating a sensor in tissue, comprising:

an external probe including electronic means for providing a horizontal rotating magnetic field;

a sensor with a distal end located in a true direction in a horizontal plane along a longitudinal axis, said sensor developing an induced signal in response to said horizontal rotating magnetic field; and means, responsive to said induced signal, for resolving the true direction of said sensor distal end along the longitudinal axis in a horizontal plane.

32. The system of claim 31 in which said means for resolving the true direction of said sensor distal end along the longitudinal axis in a horizontal plane is further responsive to said electronic means for providing a horizontal rotating magnetic field.

33. A method of externally locating a sensor in tissue, comprising the steps of:

providing a horizontal rotating magnetic field generated electronically from a probe external to the tissue;

developing, from a sensor in the tissue and located at a relative angular orientation in a horizontal plane to the probe, and at a relative distance from the probe, an induced signal having a relative strength, in response to said horizontal rotating magnetic field;

determining the relative strength of said induced signal, independently of the relative angular orientation in the horizontal plane of said probe and said sensor; and indicating, in response to the induced signal, the relative distance between the probe and the sensor.

34. A method of externally locating a sensor in tissue, comprising:

placing in the tissue a sensor having a distal end located at a true direction along a longitudinal axis in a horizontal plane;

providing from a probe external to the tissue a horizontal rotating magnetic field;

developing from the sensor within the tissue an induced signal in response to said horizontal rotating magnetic field; and resolving and displaying, in response to said induced signal, the true direction of the sensor distal end along the longitudinal axis in a horizontal plane.

35. The method of claim 34 in which the horizontal rotating magnetic field and the induced signal have phases, and in which resolving and displaying the true direction of the sensor distal end along the longitudinal axis in a horizontal plane includes comparing the phase of the induced signal to the phase of the horizontal rotating magnetic field.

* * * * *